United States Patent [19]

Nakagaki et al.

[11] Patent Number: 4,670,206
[45] Date of Patent: Jun. 2, 1987

[54] METHOD AND APPARATUS FOR SOLIDIFYING A POWDERED COSMETIC COMPOSITION IN AN ELONGATED HOLLOW CONTAINER

[75] Inventors: Tomonari Nakagaki, Mitaka; Yoshiharu Sekimoto, Machida; Mamoru Ishii, Sagamihara; Haruo Ishibashi, Hatano, all of Japan

[73] Assignee: Asanuma Sogyo Kabushiki Kaisha, Tokyo, Japan

[21] Appl. No.: 738,335

[22] Filed: May 28, 1985

[30] Foreign Application Priority Data

Jun. 25, 1984 [JP] Japan ................. 59-130669

[51] Int. Cl.⁴ ............................................. B28B 1/26
[52] U.S. Cl. ................................... 264/87; 264/37; 264/71; 264/122; 264/267; 264/297.8; 425/84; 425/110; 425/432; 425/434; 425/DIG. 32
[58] Field of Search ............ 264/37, 87, 69, 71, 264/86, 267, 297.8, 330, 117, 122; 249/113, 141; 424/63, 64, 69, DIG. 5; 425/84, 110, 432, 434, 456, 570, 571, 572, 588, DIG. 32

[56] References Cited

U.S. PATENT DOCUMENTS

| | | | |
|---|---|---|---|
| 1,963,030 | 6/1934 | Powell | 264/37 |
| 3,839,521 | 10/1974 | Robinson | 264/87 |
| 4,332,763 | 6/1982 | Hempel et al. | 264/330 X |

FOREIGN PATENT DOCUMENTS 308626  3/1929  United Kingdom ............ 264/87

Primary Examiner—Jan H. Silbaugh
Assistant Examiner—Leo B. Tentoni
Attorney, Agent, or Firm—Armstrong, Nikaido, Marmelstein & Kubovcik

[57] ABSTRACT

A method and apparatus for solidifying a powdered cosmetic composition in a vertically held elongated hollow container to form a stick-shaped powdered cosmetic. A dispersion of the powdered cosmetic composition in a liquid phase is filled in the container. Pneumatic pressure is applied to the upper surface of the dispersion, and at the same time, the liquid phase contained in the dispersion is removed from below a screen placed at the lower end of the container.

8 Claims, 2 Drawing Figures

METHOD AND APPARATUS FOR SOLIDIFYING A POWDERED COSMETIC COMPOSITION IN AN ELONGATED HOLLOW CONTAINER

BACKGROUND OF THE INVENTION

This invention relates to a novel method of, and a novel apparatus for, solidifying a powdered cosmetic composition consisting essentially of powdered cosmetic ingredients in an elongated hollow container to form a stick-shaped powdered cosmetic.

The solidified powder of this type is used for various purposes. For example, a compact is made by compressing the powder in a receptacle with a compressing plate. At the time of use, a bar having a sponge-like member at its end is used for applying the powder. This mode of application has a disadvantage in that the powder particles tend to scatter during application.

To avoid this scattering of particles, a pencil-shaped product having in a wooden case a core molded in the shape of a stick from powder kneaded with wax, oil, or the like has been proposed. Although no scattering of particles occurs upon application of these types of cosmetics, they have the following disadvantages when compared to a solidified powdered cosmetic composition: they fail to spread well, and do not maintain a cosmetic effect for a long time.

Another product in the shape of a stick has been formed by solidifying a powdered cosmetic composition with plaster. However, this product has a short pot life and is difficult to manufacture because plaster hardens rapidly. Moreover, it lacks uniformity in quality and feels rough.

Another product which is in the shape of a stick or pencil has been made by using a water-soluble binder with a powdered cosmetic composition. This composition is kneaded, then molded by compression into a stick of a given diameter, and dried. The drying step tends to be time-consuming. A pencil-shaped product is manufactured by an undesirably complicated process wherein this stick is clamped with stick splints to form it into a pencil shape.

In view of the foregoing, applicants have completed this invention which is believed to be very beneficial in that it enables the solidification of powder in situ in a pencil-shaped container.

SUMMARY OF THE INVENTION

One object of this invention is to provide an easy method for solidifying a powdered cosmetic composition in a vertically supported elongated hollow container with open ends such as a pencil-shaped container. The container is filled with a dispersion of the powdered cosmetic composition in a liquid phase (that is, a liquid dispersion medium). Such dispersion is in the form of a slurry. Pneumatic pressure is applied to the whole upper surface of the dispersion, whereby the liquid phase of the dispersion is forced downward and is removed from the container so that only the powdered composition remains and is solidified in the container.

According to another object of this invention, there is provided an apparatus which is used for carrying out the method of this invention. Such apparatus includes a support means on which are held vertically a plurality of elongated hollow containers having open ends wherein a dispersion of the powdered cosmetic composition in a liquid phase is received. A vessel provided with means for injecting the dispersion into the containers and means for applying air pressure to the upper surface of the dispersion in the containers is disposed immediately above the containers and holds an appropriate amount of the dispersion. A screen means is disposed at the bottom of the support. A packing which is resistant to the liquid phase in the dispersion is provided under the screen means, said packing having holes which define passages for the liquid phase. A liquid phase receptacle is disposed below the packing, such receptacle having an opening to the atmosphere and being connected to a discharging device so that the liquid phase may be discharged and recovered. The support means on which the containers are vertically held may be replaced by a support means which includes means for vibrating said containers.

DETAILED DESCRIPTION OF THE INVENTION

Figure 1:
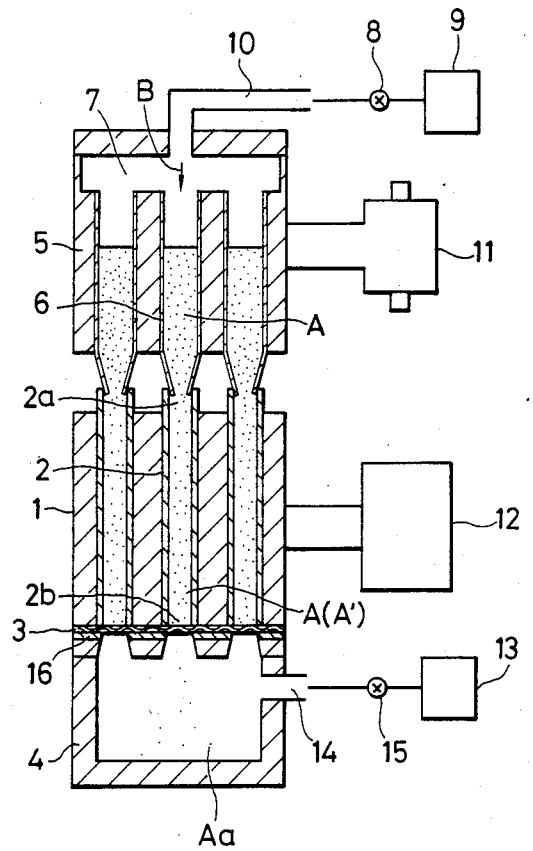
FIG. 1 is a cross-sectional view showing one example of the apparatus according to the present invention.

In the method of this invention for solidifying a powdered composition in a pencil-shaped container, the container is filled with an appropriate amount of a dispersion of the powdered cosmetic composition in a liquid phase, pneumatic pressure is applied to the whole upper surface of the dispersion in the container, and the liquid phase of the dispersion is simultaneously removed through a screen means disposed under the container.

The following liquids are suitable for the liquid phase in this invention; water; organic solvents including hydrocarbons (such as n-hexane, n-heptane, low-boiling point isoparaffin, fluorohydrocarbons, etc.), alcohols (such as ethanol, isopropanol, etc.), ethers or acetals (such as isopropylether, tetrahydrofuran, diethylacetal, etc.), ketones (such as acetone, methylethylketone, etc.), esters (such as ethylacetate, ethyl lactate, etc.), polyalcohols or derivatives thereof (such as ethylene glycol monoethylether, propylene glycol, ethylene glycol monoethylether, propylene glycol, ethylene glycol monoethyl ether acetate, etc.), volatile silicones (such as cyclic dimethylpolysiloxane, chained dimethylpolysiloxane, etc.), and mixtures of water and any of the above-mentioned organic solvents.

This invention provide an easy method for manufacturing pencil-shaped solidified powder products of uniform density. If the end of the pencil-shaped product is appropriately sharpened, it can immediately be used to apply powder uniformly to the surface to be coated. In the event the powdered cosmetic composition in the pencil retains a slight amount of residual liquid phase, this liquid phase can be removed completely by drying or vacuum drying at a temperature which is commensurate with the boiling point of the liquid phase. This complete removal of the liquid phase increases the strength of the solidified powdered composition and gives a strong powder core.

The apparatus of this invention includes a support means on which are held vertically a plurality of elongated hollow containers with open ends wherein a dispersion of a powdered composition in a liquid phase is received; a vessel for holding an appropriate amount of the dispersion disposed immediately above the containers and provided with means for injecting said dispersion into the containers and means for applying pneumatic pressure on the whole upper surface of said dispersion; a screen means disposed at the bottom of the support means; packing means provided under the screen means and having holes defining passages for the liquid phase of the dispersion, said packing means being chemically resistant to this liquid phase; and a liquid phase receptacle disposed below the packing means having an opening which is open to the atmosphere, said liquid phase receptacle being connected to a discharging device so that the liquid phase may be discharged and recovered.

The powdered cosmetic compositions to be solidified by means of the present apparatus are, for example, an eye shadow, an eyebrow cosmetic, an eye liner, a rouge, a foundation or other pencil-shaped cosmetics.

An example of the apparatus according to the present invention is shown in FIG. 1, it being understood that the apparatus of this invention is not limited to the specifically described embodiment.

A support 1 is provided for supporting vertically a plurality of pencil-shaped containers 2 each having a top opening 2a and a bottom opening 2b and an appropriate wall thickness. A 200 to 350 mesh screen 3 of, for example, stainless steel, nylon or TEFLON, is provided at the bottom of the support 1 and closes the bottom openings 2b of the containers 2. Liquid phase-resistant packing 16 is disposed under the screen 3 and has holes defining passages for the liquid phase. A liquid phase receptacle 4 is connected to the support 1 below the packing 16 for receiving the liquid phase, and has an opening 14 which is open to the atmosphere. A vessel 5 is disposed above the support 1 and has a plurality of injecting nozzles 6 each having a lower end which can be brought into intimate contact with the top opening 2a of one of the containers 2. The vessel 5 has adjacent to its top a hollow chamber 7 to which one end of an air conduit 10 is connected, while the other end thereof is connected to a compressor 9. The air conduit 10 is provided with a valve 8. A device 11 is provided for effecting the vertical sliding movement of the vessel 5. A device 12 is connected to the support 1 for vibrating it. A discharging device 13, such as a pump, is connected to the opening 14 of the liquid phase receptacle 4 and a valve 15 is provided between the device 13 and the opening 14.

In the process of solidifying a powdered composition according to this invention and using the above-mentioned apparatus, the vessel 5 is lowered by the device 11 so that the lower ends of the injection nozzles 6 projecting downwardly from the vessel 5 may be brought into intimate contact with the top openings 2a of the pencil-shaped containers 2, respectively, mounted in the support 1. An appropriate amount of dispersion of powdered cosmetic composition A in a liquid phase is charged by a charger (not shown in FIG. 2) into each injection nozzle 6 and thereby into the corresponding pencil-shaped container 2 connected therewith.

The discharging device 13 is driven and the valve 15 is opened. The vibrating device 12 is driven to vibrate the support 1 thereby shaking the whole dispersion of powdered cosmetic composition A to prevent its dilatancy and to distribute it uniformly. The compressor 9 is driven and the valve 8 is opened to supply compressed air B into the hollow chamber 7 through the conduit 10. The compressed air applies pressure to the whole surface of the dispersion A in the injection nozzle 6. This pressure squeezes the liquid phase Aa out of the dispersion A in the containers 2, and the liquid phase Aa drops into the liquid phase receptacle 4 through the screen 3, whereby a stick A' of uniformly solidified powdered cosmetic composition is formed in each container 2.

Even if the vibrating device 12 is omitted, the compressed air pressure is sufficient to enable the satisfactory formation of solidified products, although it may be necessary to apply air pressure to the powdered cosmetic composition for a somewhat longer time.

Figure 2:
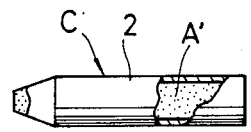
FIG. 2 is a side elevational view, partly in section, of the product obtained by the present invention.

Finally, the pencil-shaped containers 2 holding the sticks of powdered cosmetic composition A' therein are removed from the support 1 and processed appropriately to yield powder sticks. The thus obtained stick of powdered cosmetic composition is indicated as "C" and is shown in FIG. 2.

As described above, the method of, and the apparatus for, solidifying a powdered cosmetic composition in a pencil-shaped container according to the present invention are especially simple. The method can be easily carried out by compressing a dispersion of the powdered cosmetic composition in a liquid phase with air pressure and, at the same time, removing the liquid phase contained in said dispersion, whereby obtaining pencil-shaped solidified products with uniformity and excellent strength.

Accordingly, the complexity found in conventional methods has been removed, and the present invention provides an excellent method and apparatus for solidifying a powdered cosmetic composition in pencil-shaped containers.

The followings are examples of the powdered cosmetic compositions to be solidified by the present apparatus, in which "parts" means "parts by weight".

Example 1: Eye shadow

| | |
|---|---|
| Mica titanium | 95 parts |
| Bentone 38 | 5 parts |
| Perfume | quantity suitable |
| Ethanol | 400 parts |

Example 2: Eye shadow

| | |
|---|---|
| Amino acid-treated titanium mica | 95 parts |
| Bentone 38 | 5 parts |
| Perfume | quantity suitable |
| Fronsolve AE*[1] | 400 parts |

*[1]"Fronsolve AE" is a commercially available volatile fluorohydrocarbon made by Asahi Glass Co. (Japan).

Example 3: Rouge

| | |
|---|---|
| Silicone-treated mica | 22 parts |
| Silicone-treated titanium mica | 22 parts |
| Silicone-treated talc | 34 parts |
| Silicone-treated inorganic pigment | 8 parts |
| Silicone-treated color pigment | 2.7 parts |
| Zinc stearate | 10 parts |
| S-ben | 1.3 parts |
| Perfume | quantity suitable |
| Antiseptic | quantity suitable |
| CG Trifron A*[2] | 300 parts |

*[2]"CG Trifron A" is a commercially available volatile fluorohydrocarbon made by Asahi Glass Co. (Japan).

Example 4: Foundation

| | |
|---|---|
| Metallic soap-treated talc | 50 parts |
| Metallic soap-treated sericite | 10 parts |
| Metallic soap-treated mica | 20 parts |
| Silicone-treated titanium oxide | 6 parts |
| Silicone-treated red iron oxide | 2.3 parts |
| Zinc stearate | 10 parts |
| Bentone 27*[3] | 1.7 parts |
| Fronshowa FS-3*[4] | 500 parts |

*[3]"Bentone" is a commercially available organic bentonite made by National Lead Industries, Inc. (USA).
*[4]"Fronshowa FS-3" is a commercially available volatile fluorohydrocabon made by Showa Denko Co. (Japan).

What is claimed is:

1. An apparatus for solidifying a powdered cosmetic composition in a container comprising:
   support means for supporting in a vertical position a plurality of elongated hollow containers, each container being provided with a top opening and a bottom opening,
   a vessel for holding a dispersion of the powdered cosmetic composition in a liquid dispersion medium, said vessel being provided with injection nozzles corresponding in number to the plurality of elongated hollow containers and respectively facing and being engageable with the top openings of the containers for charging the dispersion into the containers, said vessel being further provided with means for applying pneumatic pressure to the upper surface of the dispersion to force the liquid dispersion medium to flow downward out of the dispersion held in the elongated hollow containers,
   screen means positioned at the bottom openings of the elongated hollow containers, and
   a receptacle below said screen means for receiving the liquid medium forced out of the dispersion.

2. An apparatus as in claim 1 further comprising means for vertically moving said vessel.

3. An apparatus as in claim 1 further comprising means for vibrating said support means.

4. An apparatus as in claim 1 further comprising a liquid discharging device connected to the receptacle.

5. An apparatus for solidifying a powdered cosmetic composition in a pencil-shaped container comprising:
   (a) a support for mounting vertically a plurality of pencil-shaped containers each having a top opening and a bottom opening;
   (b) a vessel disposed immediately above the support and having a plurality of nozzles corresponding in number to the plurality of containers respectively facing and being engageable with the top openings of the pencil-shaped containers, each nozzle holding an appropriate amount of a dispersion of said powdered cosmetic composition in a solvent, and means for applying air pressure to the upper surface of said dispersion;
   (c) a screen disposed at the bottom openings of said pencil-shaped containers;
   (d) packing disposed under said screen, said packing being resistant to the liquid phase contained in the dispersion and having holes defining passages for the liquid phase;
   (e) a liquid phase receptacle disposed below said packing, and
   (f) a liquid phase discharging device connected to said receptacle.

6. An apparatus as in claim 5, wherein said support includes means for vibrating said plurality of containers.

7. A method for solidifying a powdered cosmetic composition in a container comprising the steps of:
   supporting in a vertical position a plurality of elongated hollow containers on a support means, each container being provided with a top opening and a bottom opening;
   disposing a dispersion-charging vessel on top of the elongated hollow containers, said vessel containing a dispersion of the powdered cosmetic composition in a liquid dispersion medium in an amount which is sufficient for filling up the elongated hollow containers, said vessel being provided with injection nozzles which correspond in number of the plurality of elongated hollow containers and respectively face and are engageable with the top openings of said containers, said vessel being further provided with means for applying pneumatic pressure to the upper surface of the dispersion to force the liquid dispersion medium to flow downward out of the dispersion held in the elongated hollow containers;
   charging the dispersion of powdered cosmetic composition into the elongated hollow containers by bringing said nozzles respectively into intimate contact with the top openings of the hollow containers; and
   forcing out the liquid dispersion medium from the dispersion through a screen means positioned at the bottom openings of the hollow containers by applying said pneumatic pressure to the upper surface of the dispersion.

8. A method as in claim 7, wherein said powdered cosmetic composition is selected from the group consisting of eye shadow, eyebrow cosmetic, eye liner, rouge, foundation or other pencil-shaped cosmetics.

* * * * *